US012690906B2

(12) United States Patent
Stroh

(10) Patent No.: US 12,690,906 B2
(45) Date of Patent: Jul. 28, 2026

(54) SURGICAL CEMENT REMOVAL TOOL

(71) Applicant: Shukla Medical, St. Petersburg, FL (US)

(72) Inventor: Austin Ryan Stroh, Lutz, FL (US)

(73) Assignee: Shukla Medical, St. Petersburg, FL (US)

( * ) Notice: Subject to any disclaimer, the term of this patent is extended or adjusted under 35 U.S.C. 154(b) by 325 days.

(21) Appl. No.: 18/158,191

(22) Filed: Jan. 23, 2023

(65) Prior Publication Data

US 2023/0240734 A1     Aug. 3, 2023

Related U.S. Application Data

(60) Provisional application No. 63/304,030, filed on Jan. 28, 2022.

(51) Int. Cl.
*A61B 17/88*        (2006.01)
*A61B 17/16*        (2006.01)

(52) U.S. Cl.
CPC ...... *A61B 17/8847* (2013.01); *A61B 17/1604* (2013.01)

(58) Field of Classification Search
CPC ................................................ A61B 17/8847
See application file for complete search history.

(56) References Cited

U.S. PATENT DOCUMENTS

| | | | | |
|---|---|---|---|---|
| 5,536,266 A | * | 7/1996 | Young | A61B 17/8847 |
| | | | | 606/92 |
| 6,065,188 A | * | 5/2000 | Wold | A47J 45/06 |
| | | | | 16/436 |
| 10,327,827 B2 | * | 6/2019 | Young | A61B 17/1659 |
| 2020/0352579 A1 | | 11/2020 | Davis et al. | |

FOREIGN PATENT DOCUMENTS

| | | |
|---|---|---|
| RU | 175326 U1 | 11/2017 |
| WO | 1992022259 A2 | 12/1992 |
| WO | 2020065245 A1 | 4/2020 |

OTHER PUBLICATIONS

Extended European Search Report and Written Opinion dated May 25, 2023 in counterpart European Application No. 23153557.6.

* cited by examiner

*Primary Examiner* — Andrew Yang
(74) *Attorney, Agent, or Firm* — Kim IP Law Group LLC

(57)     ABSTRACT

A surgical cement removal tool including an elongated shaft having a proximal end and a distal end, and a bowl-shaped scoop affixed to the distal end. Handle attachment structure can be provided adjacent the proximal end of the elongated shaft to permit releasable attachment of the surgical cement removal tool to a handle. Alternatively, the proximal end of the elongated shaft may be permanently affixed to a suitable handle.

20 Claims, 9 Drawing Sheets

112

SURGICAL CEMENT REMOVAL TOOL

CROSS-REFERENCE TO RELATED APPLICATIONS

This application claims the benefit under 35 U.S.C. § 119(e) to U.S. Provisional Application No. 63/304,030, filed Jan. 28, 2022, the entire disclosure of which is hereby incorporated by reference for all purposes.

BACKGROUND OF THE DISCLOSURE

Exemplary embodiments of the subject disclosure relate generally to the field of surgical cement removal tools. Specifically, the subject disclosure relates to a surgical chisel.

Oftentimes when performing an implant revision surgery it becomes necessary or desirable to remove surgical cement from the implant area. The subject disclosure provides an improved surgical cement removal tool in the form of a surgical chisel to address this need.

SUMMARY OF THE DISCLOSURE

According to an exemplary embodiment of the subject disclosure, there is provided a surgical cement removal tool comprising an elongated shaft having a proximal end and a distal end, and a bowl-shaped scoop affixed to the distal end.

According to an aspect, the bowl-shaped scoop is concentrically arranged with respect to a central longitudinal axis of the elongated shaft. According to another aspect, the bowl-shaped scoop has a proximally directed open side. According to another aspect, the open side of the bowl-shaped scoop has a proximal end including a cutting edge about a perimeter thereof. According to another aspect, the cutting edge extends 360 degrees about the perimeter of the proximal end of the open side. According to another aspect, the cutting edge is contiguous with a sloped surface disposed at an acute angle with respect to the longitudinal axis of the elongated shaft, whereby surgical cement removed from a bone cannula falls into the bowl-shaped scoop. Surgical cement may be removed from the scoop upon withdrawal of the surgical cement removal tool from the bone cannula.

According to an aspect, the surgical cement removal tool further comprises a handle connected to the proximal end of the elongated shaft. According to another aspect, the surgical cement removal tool further comprises handle attachment structure adjacent the proximal end of the elongated shaft to permit releasable attachment of the surgical cement removal tool to the handle. According to another aspect, the proximal end of the elongated shaft is fixedly connected to the handle. According to another aspect, a circumference of the elongated shaft is sized to be received within a slot of a slotted hammer, whereby the hammer may be used to strike a distal end of the handle and exert proximally directed force on the handle and thus the elongated shaft and the cutting edge of the bowl-shaped scoop such that the cutting edge scrapes surgical cement from an inner wall of a bone cannula.

BRIEF DESCRIPTION OF THE SEVERAL VIEWS OF THE DRAWINGS

The following detailed description of an exemplary embodiment of the subject disclosure will be better understood when read in conjunction with the appended drawings. For the purpose of illustrating the present disclosure, there is shown in the drawings an exemplary embodiment. It should be understood, however, that the subject application is not limited to the precise arrangements and instrumentalities shown.

DETAILED DESCRIPTION

Reference will now be made in detail to an exemplary embodiment of the subject disclosure illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as upper, lower, top, bottom, above, below and diagonal, are used with respect to the accompanying drawings. Such directional terms used in conjunction with the following description of the drawings should not be construed to limit the scope of the subject disclosure in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art. "Exemplary" as used herein shall mean serving as an example.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

Figure 1:
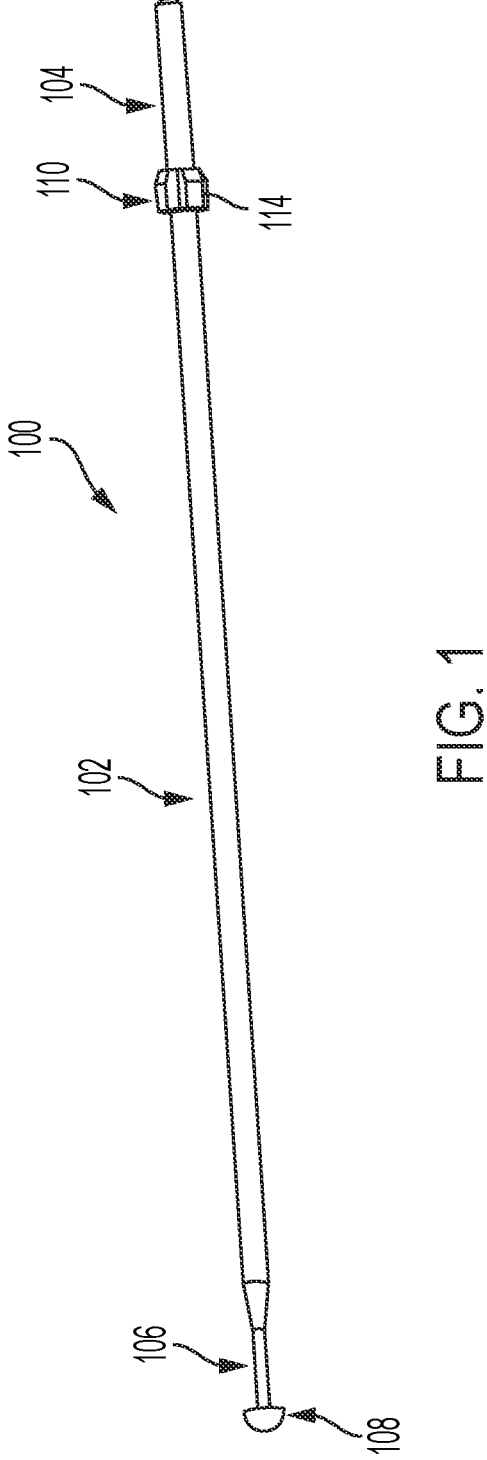
FIG. 1 is a perspective view of a surgical cement removal tool in accordance with an exemplary embodiment of the subject disclosure.
Figure 2:
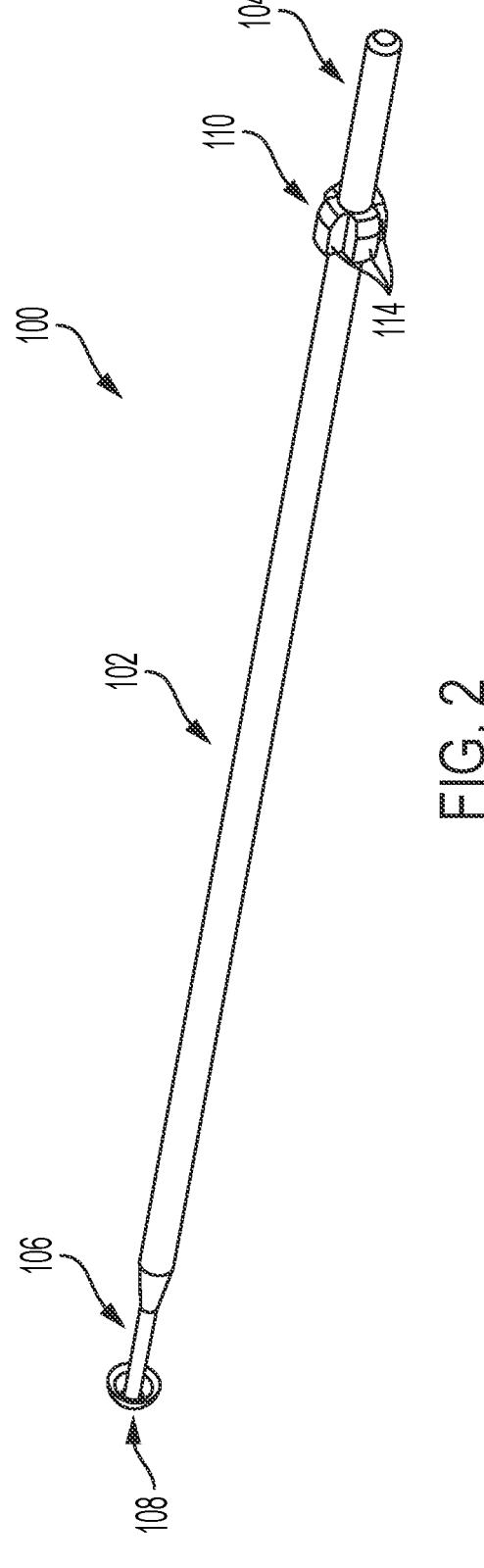
FIG. 2 is another perspective view of the surgical cement removal tool of FIG. 1.
Figure 3:
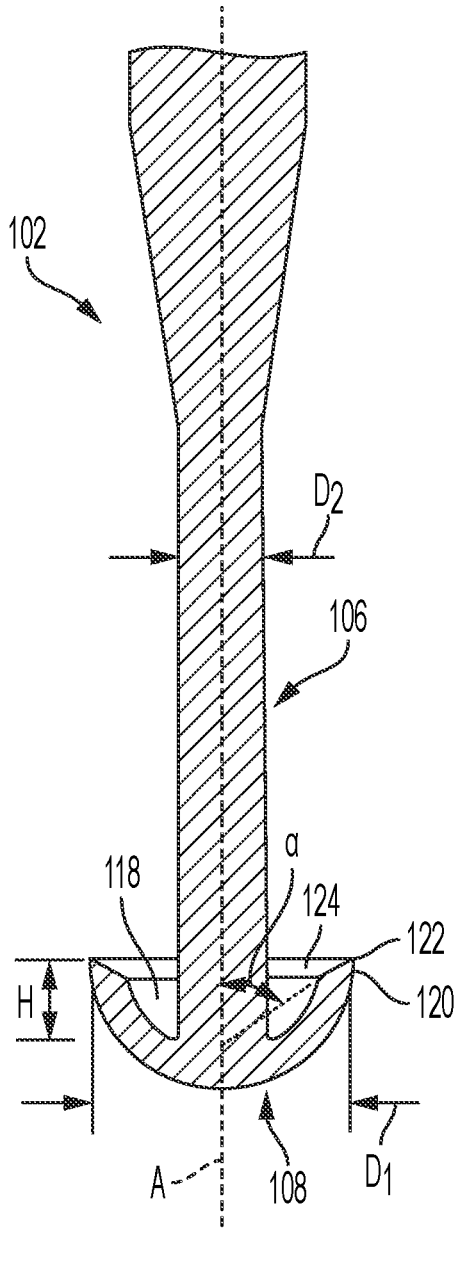
FIG. 3 is an enlarged cross-sectional view of a distal end of the surgical cement removal tool of FIG. 1.
Figure 4:
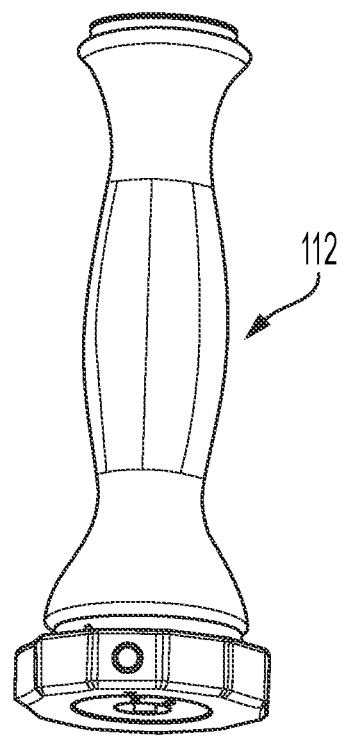
FIG. 4 is a perspective view of a handle to which the surgical cement removal tool of FIG. 1 may be attached.
Figure 5:
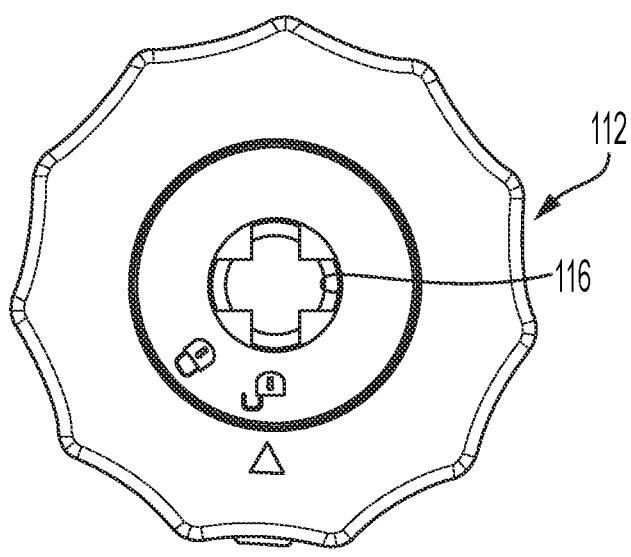
FIG. 5 is a distal end view of the handle of FIG. 4.
Figure 6:
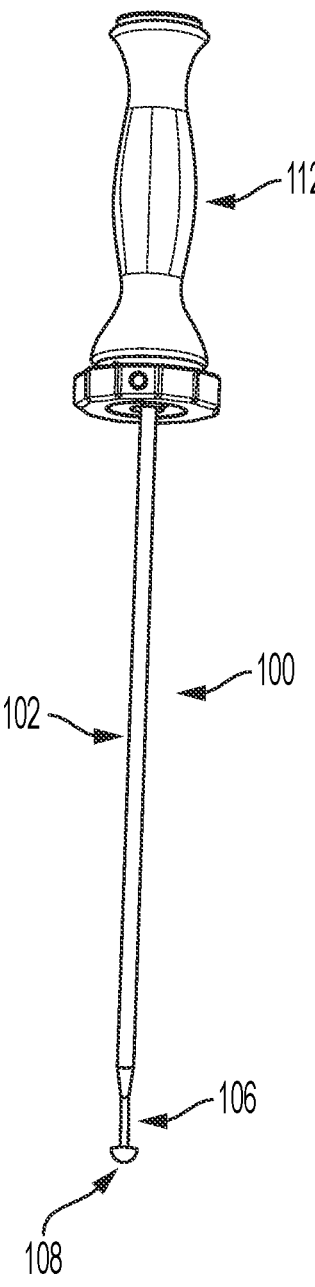
FIG. 6 is a side view of the surgical cement removal tool of FIG. 1 attached to the handle of FIG. 4.

Referring now to the drawings, FIGS. 1-3 illustrate a surgical cement removal tool 100 according to an exemplary embodiment of the present disclosure. As described in greater detail below, the surgical cement removal tool functions in the manner of a chisel. The surgical cement removal tool 100 includes an elongated shaft 102 having a proximal end 104 and a distal end 106, and a bowl-shaped scoop 108 affixed to the distal end 106. The elongated shaft may be from about 8 to 9 inches in length but may be of lesser or greater length, e.g., 6, 7, 10 or 11 inches. Handle attachment structure 110 can be provided adjacent the proximal end of the elongated shaft to permit releasable attachment of the surgical cement removal tool 100 to a handle 112 (FIGS. 4 and 6). The handle attachment structure 110 comprises at least one radially projecting key 114 which is sized to be received in a correspondingly-shaped opening 116 provided in a distal end of the handle 112 (FIG. 5). According to an aspect, the handle 112 may be constructed and arranged to releasably lock the elongated shaft to the handle in the manner disclosed in U.S. patent application Ser. Nos. 17/451,665 and 16/549,896, the entire disclosures of which are hereby incorporated by reference for all purposes. Alternatively, the proximal end 104 of the elongated shaft may be permanently affixed to a suitable handle such as by welding, adhesive, or the like.

As best shown in FIG. 3, the bowl-shaped scoop 108 is desirably concentrically arranged with respect to a central longitudinal axis A of the elongated shaft 102. The bowl-shaped scoop has a proximally directed open side 118. The open side of the bowl-shaped scoop has a proximal end 120 provided with a cutting edge 122 about a perimeter thereof. According to an aspect, the cutting edge preferably extends 360 degrees about the perimeter of the proximal end of the open side of the bowl-shaped scoop. The cutting edge is contiguous with a sloped surface 124 disposed at an acute angle α with respect to the longitudinal axis A of the elongated shaft, whereby surgical cement removed from a bone cannula by the cutting edge 122 falls into the bowl-shaped scoop, as described in connection with FIG. 7. The bowl-shaped scoop may have an outer diameter $D_1$ of about 0.375 inches and a depth H of about 0.18 inches. In addition, the distal end 106 of the elongated shaft 102 can have a diameter $D_2$ of about 0.125 inches.

Figure 7:
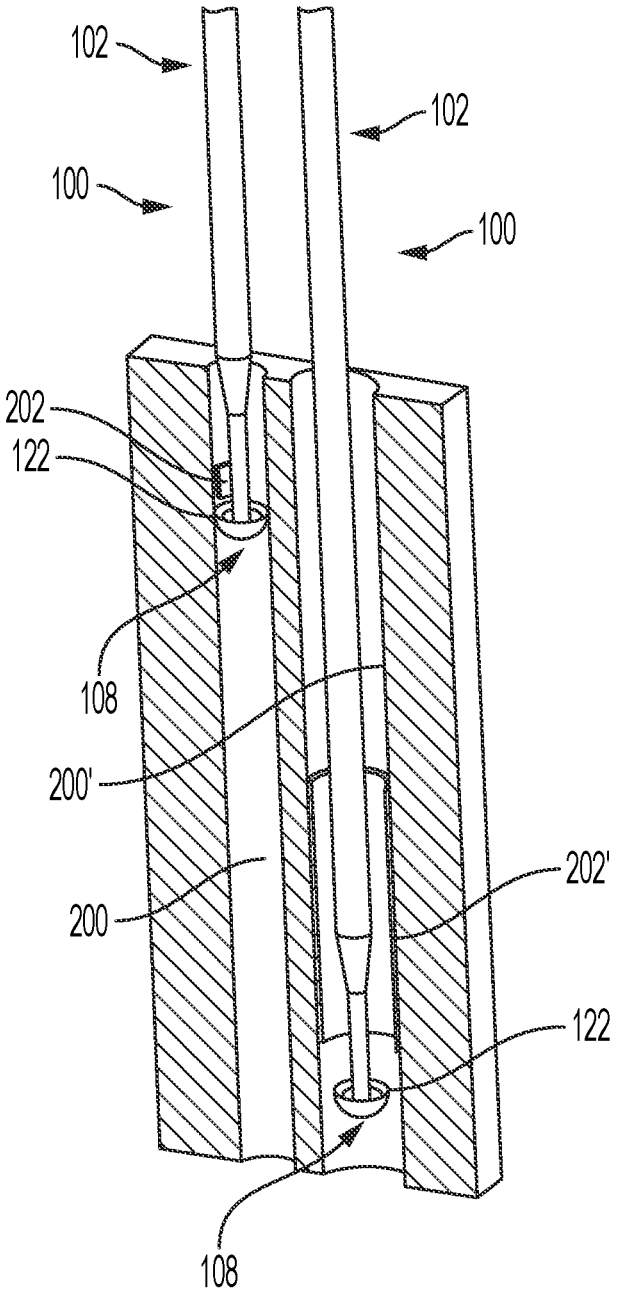
FIG. 7 is a composite cross-sectional view of two bone cannulas with the surgical cement removal tool of FIG. 1 shown deployed therein.

Referring to FIG. 7, there is shown a composite cross-sectional view of two bone canals or cannulas 200, 200' with the surgical cement removal tool 100 shown deployed therein. Depending on the extent of surgical cement present in in cannula 200 or cannula 200', the surgical cement removal tool 100 may be used by itself to remove cement from the walls of the cannula. However, if considerable surgical cement is present, the surgical cement removal tool 100 may be used after other chisel(s) have removed sufficient cement to permit passage of the bowl-shaped scoop 108 into the cannula.

Referring first to cannula 200, a small piece of surgical cement 202 is shown remaining on the wall of the cannula such as might be the case after other chisels have removed the majority of the cement from the cannula. In this example, the surgical cement is located approximately one inch from the upper opening of the cannula 200. The bowl-shaped scoop 108 is inserted into the cannula 200 until the 360 degree cutting edge 122 is beneath the lowest extent of the surgical cement 202. With the cutting edge 122 so situated, a user then pulls upwardly on the handle 112 (FIGS. 4 and 6) in order to scrape the cutting edge 122 against the surgical cement 202 such that the loosened cement falls into the bowl-shaped scoop. Even in areas of limited visibility the 360 degree cutting edge 122 makes it easy for a user to remove the cement from the wall of the cannula. Surgical cement may be removed from the scoop upon withdrawal of the surgical cement removal tool from the bone cannula. The process is repeated until a desired amount of cement is removed from the wall of the cannula 200.

Referring to cannula 200', which is larger in diameter than cannula 200, there is shown a thin layer of cement 202' which is of larger area than the piece of surgical cement 202 of cannula 200. In addition, cement 202' is located deeper in the cannula 200' than cement 202 is located in the cannula 200. The bowl-shaped scoop 108 is inserted into the cannula 200' until the 360 degree cutting edge 122 is beneath the lowest extent of the surgical cement 202'. Indeed, the bowl-shaped scoop 108 is inserted into the cannula as deep as is necessary until the handle 112 contacts the bone. With the bowl-shaped scoop in proper position, the user again pulls upwardly on the handle 112 (FIGS. 4 and 6) in order to scrape the cutting edge 122 against the surgical cement 202' such that the loosened cement falls into the bowl-shaped scoop. Again, the process is repeated until a desired amount of cement is removed from the wall of the cannula 200.

Figure 8:
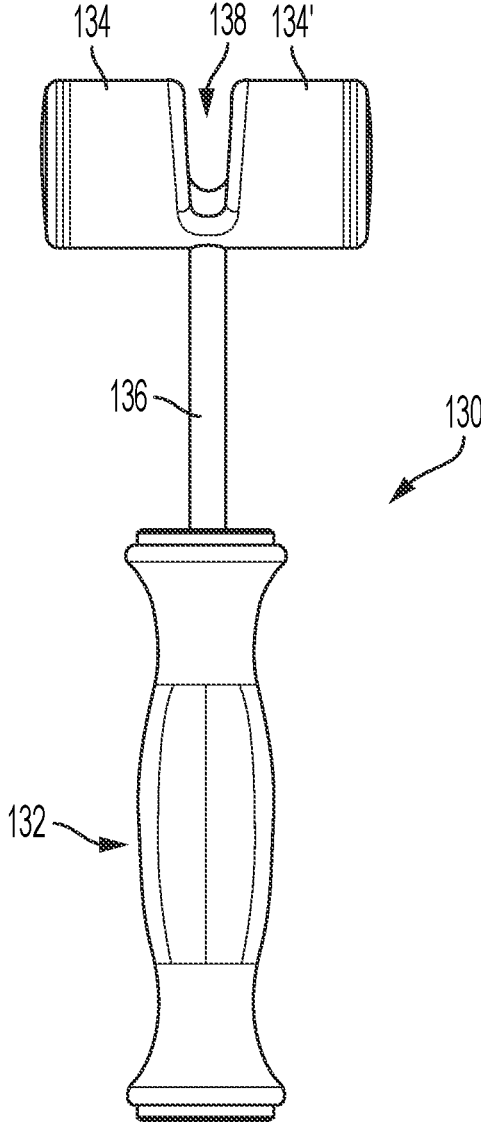
FIG. 8 is a side view of a surgical hammer suitable for use with surgical cement removal tool of FIG. 1 and the handle of FIG. 4.
Figure 9:
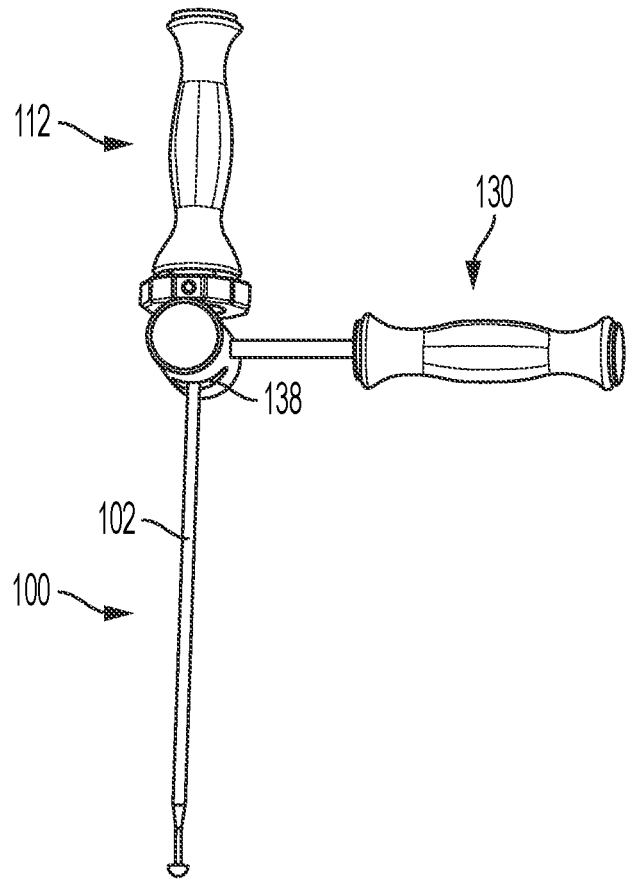
FIG. 9 is a perspective view of the surgical cement removal tool of FIG. 1 attached to the handle of FIG. 4 with the elongated shaft of the surgical cement removal tool received within a slot of the surgical hammer of FIG. 8.

If the cement 202, 202' is firmly adhered to the walls of the cannulas 200, 200' and resists removal by mere manipulation of the handle 112, the user may use a slotted hammer 130 (FIGS. 8 and 9) to strike the distal end of the handle 112 to generate additional cement removing force at the cutting edge 122. In this regard, the slotted hammer 130 includes a handle 132 and a bifurcated head 134, 134' joined by a shaft 136. The bifurcated head 134, 134' is divided by a slot 136. According to an aspect, the slotted hammer 130 may be constructed and in the manner disclosed in U.S. patent application Ser. No. 16/787,500 the entire disclosure of which is hereby incorporated by reference for all purposes. A circumference of the elongated shaft 102 of the surgical cement removal tool 100 is sized to be received within the slot 136, as best shown in FIG. 9. With the hammer positioned as shown in FIG. 9, the user can rapidly lower and raise the bifurcated head of the hammer to strike a distal end of the handle 112 to exert enhanced cement removing force at the cutting edge 122 to dislodge the surgical cement from the wall of the bone cannula.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the claims defined herein.

The invention claimed is:

1. A surgical cement removal tool comprising:
   a bowl-shaped scoop having a notchless, longitudinally continuously convex exterior surface and a proximally directed interior open side;
   an elongated shaft having a proximal end and a distal end, the distal end of the elongated shaft being affixed to the interior open side of the bowl-shaped scoop.

2. The surgical cement removal tool of claim 1, wherein the bowl-shaped scoop is concentrically arranged with respect to a central longitudinal axis of the elongated shaft.

3. The surgical cement removal tool of claim 1, wherein the open side of the bowl-shaped scoop has a proximal end including a cutting edge about a perimeter thereof.

4. The surgical cement removal tool of claim 3, wherein the cutting edge extends 360 degrees about the perimeter of the proximal end of the open side.

5. The surgical cement removal tool of claim 3, wherein the cutting edge is contiguous with a sloped surface disposed at an acute angle with respect a central longitudinal axis of the elongated shaft.

6. The surgical cement removal tool of claim 1, further comprising handle attachment structure adjacent the proximal end of the elongated shaft for enabling releasable attachment of the surgical cement removal tool to a handle.

7. The surgical cement removal tool of claim 1, further comprising a handle connected to the proximal end of the elongated shaft.

8. The surgical cement removal tool of claim 7, wherein the proximal end of the elongated shaft is fixedly connected to the handle.

9. The surgical cement removal tool of claim 7, wherein a circumference of the elongated shaft is sized to be received within a slot of a slotted hammer, whereby the hammer is used to strike a distal end of the handle and exert proximally directed force on the handle.

10. The surgical cement removal tool of claim 1, wherein the proximally directed open side has a single concave interior surface therein.

11. The surgical cement removal tool of claim 10, wherein the concave interior and convex exterior surfaces are each concentrically arranged with a central longitudinal axis of the elongated shaft.

12. The surgical cement removal tool of claim 10, wherein the bowl-shaped scoop has a proximal end including a cutting edge about a complete perimeter thereof.

13. A surgical cement removal tool comprising:
   an elongated shaft having a proximal end and a distal end; and a bowl-shaped scoop affixed to the distal end of the elongated shaft, wherein the bowl-shaped scoop:
      has an uninterrupted and distally directed, relative to the elongated shaft, convex exterior surface over an entire hemispheric shape thereof;
      has a proximally directed open side relative to the elongated shaft, the open side having a single concave interior surface therein; and
      the concave interior and convex exterior surfaces are each concentrically arranged with a longitudinal axis of the elongated shaft.

14. The surgical cement removal tool of claim 13, wherein the bowl-shaped scoop has a proximal end including a cutting edge about a perimeter thereof.

15. The surgical cement removal tool of claim 14, wherein the cutting edge extends 360 degrees about the perimeter of the proximal end of the bowl-shaped scoop.

16. The surgical cement removal tool of claim 14, wherein the cutting edge is contiguous with a sloped surface disposed at an acute angle with respect to the longitudinal axis of the elongated shaft.

17. The surgical cement removal tool of claim 13, further comprising a handle attachment structure adjacent the proximal end of the elongated shaft for enabling releasable attachment of a handle of the surgical cement removal tool.

18. The surgical cement removal tool of claim 17, wherein the handle attachment structure includes at least one radially projecting key sized to be received in a correspondingly-shaped opening provided in a distal end of the handle, to releasably lock the elongated shaft to the handle.

19. A surgical cement removal tool comprising:
   an elongated shaft having a proximal end and a distal end; and
   a bowl-shaped scoop affixed to the distal end of the elongated shaft, wherein the bowl-shaped scoop:
      has a convex exterior surface over an entire hemispheric shape thereof;
      has a proximally directed open side relative to the elongated shaft, the open side having a shaped interior surface therein; and
      the shaped interior and convex exterior surfaces each have an apex located at a longitudinal axis of the elongated shaft.

20. The surgical cement removal tool of claim 19, wherein the convex exterior surface of the bowl-shaped scoop is uninterrupted and continuous over the entire hemispheric shape thereof.

* * * * *